United States Patent [19]
Van Der Maas

[11] Patent Number: 6,125,709
[45] Date of Patent: Oct. 3, 2000

[54] SAMPLING TUBE AND METHOD FOR MANUFACTURING SUCH SAMPLING TUBE

[75] Inventor: Marinus Frans Van Der Maas, Arnemuiden, Netherlands

[73] Assignee: SGT Exploitatie B.V., Netherlands

[21] Appl. No.: 08/886,067

[22] Filed: Jul. 2, 1997

[30] Foreign Application Priority Data

Jul. 3, 1996 [NL] Netherlands ............................ 1003492

[51] Int. Cl.$^7$ ...................................................... G01N 1/22
[52] U.S. Cl. ........................................................ 73/863.23
[58] Field of Search ............................................ 73/863.23

[56] References Cited

U.S. PATENT DOCUMENTS

| | | |
|---|---|---|
| 2,556,331 | 6/1951 | Lockhart . |
| 4,046,014 | 9/1977 | Boehringer et al. . |
| 4,170,901 | 10/1979 | Conkle et al. ................... 219/535 X |
| 5,168,068 | 12/1992 | Yanagisawa et al. .................. 436/134 |
| 5,307,694 | 5/1994 | Nolte et al. ........................... 73/863.23 |
| 5,308,483 | 5/1994 | Sklar et al. ....................... 73/863.23 X |
| 5,381,699 | 1/1995 | Dansereau et al. .............. 73/863.23 X |
| 5,574,230 | 11/1996 | Baugh .................................. 73/863.23 |
| 5,786,228 | 7/1998 | Charlton ......................... 73/863.23 X |

FOREIGN PATENT DOCUMENTS

| | | |
|---|---|---|
| 0 042 683 | 12/1981 | European Pat. Off. . |
| 0 225 520 | 6/1987 | European Pat. Off. . |
| 2 085 158 | 12/1981 | United Kingdom . |

OTHER PUBLICATIONS

Wyatt, J.R. et al., "Sampling of Submarine Atmospheres," *Journal of Aerospace.* 104: 1105–1110 (1995). month not given.

Patent Abstracts of Europe Abstract of EP 00225520A2 "Test Tube" Kretchmer, dated Jun. 16, 1987.

*Primary Examiner*—Thomas P. Noland
*Attorney, Agent, or Firm*—Dehlinger & Associates

[57] ABSTRACT

The invention relates to a sampling tube comprising a glass tube (2) with two closed ends (3), the sampling tube (1) being filled, at least over a portion of the length of the tube, with an adsorption material (4), the adsorption material (4) being confined between two gas-permeable plugs (5). According to the invention, the plugs (5) are manufactured from completely inert material and no non-inert material is present in the sampling tube. The invention further relates to a sampling tube whose ends (3) are closed off with sealing caps (6) which are manufactured from TEFLON®, the sealing caps (6) comprising an end portion (7) and a cylindrical stopper (8) integrally connected therewith, which stopper (8), at least locally, has an external diameter receivable with a proper fit in the interior of the glass tube (2), the end portion (7) having a diameter greater than the internal diameter of the glass tube (2). The invention further describes a method for manufacturing such sampling tubes.

9 Claims, 4 Drawing Sheets

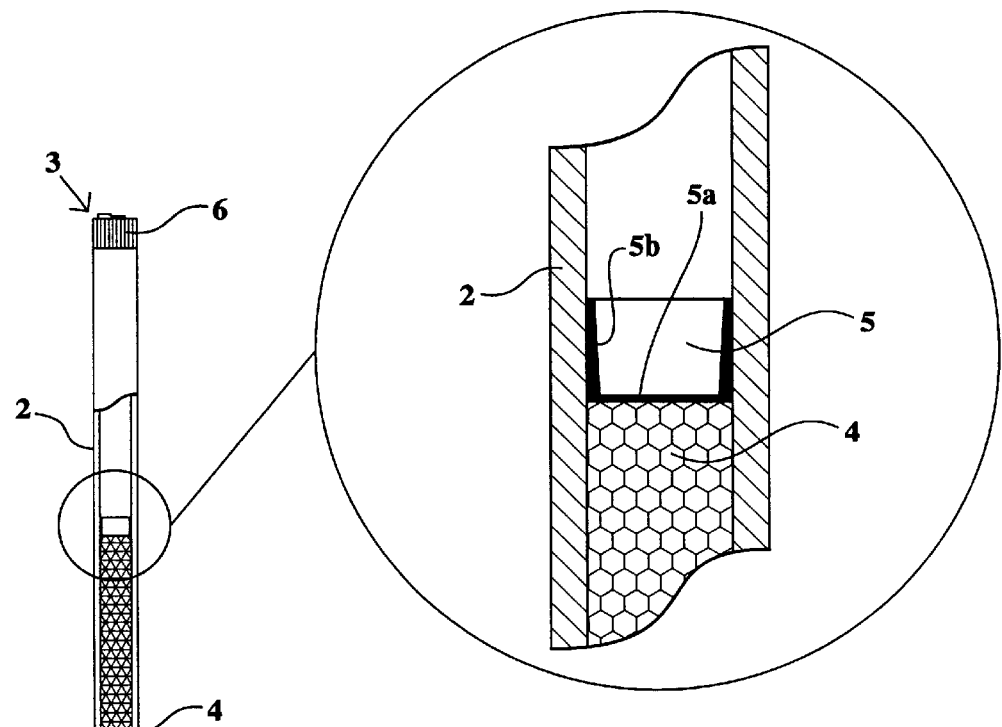
Fig. 2C
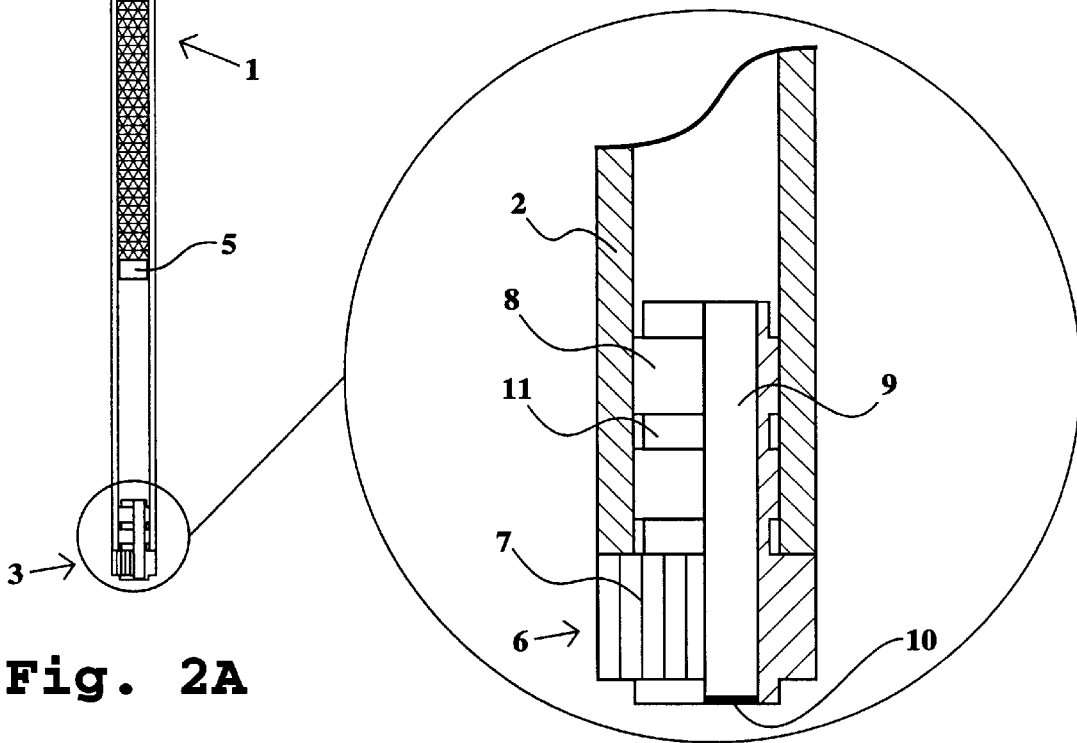
Fig. 2A
Fig. 2B

SAMPLING TUBE AND METHOD FOR MANUFACTURING SUCH SAMPLING TUBE

This application claims priority to application No. 1003492 filed in The Netherlands on Jul. 3, 1996.

FIELD OF THE INVENTION

This invention relates to a sampling tube comprising a glass tube with two closed ends, the sampling tube being filled, at least over a portion of the length of the tube, with an adsorption material, the adsorption material being confined between two gas-permeable plugs.

BACKGROUND OF THE INVENTION

Sampling tubes as described above are generally used for collecting substances contained in the air or a gas. In order to detect the amount of collected substances with a view to deriving therefrom the concentration of these substances in the air or the gas, the air or the gas is blown through the tube. The adsorption material contained in the sampling tube adsorbs a large number of substances from the air or the gas. In order to determine what substances were present in the air, the sampling tube is connected by one end, with interposition of a filtering device, to a source of inert carrier gas, such as for instance helium, and by the other end thereof to a gas chromatograph or another detection device, optionally with interposition of a cold trap. Then the filtered inert carrier gas coming from the source is pumped through the sampling tube to the detection device. When during that operation the sampling tube is heated to about 250° C., the substances adsorbed in the adsorption material are liberated again. The detection device subsequently provides a quantitative indication of the substances contained in the carrier gas. The cold trap, if any is present, serves to temporarily freeze all substances released by the sampling tube. When the cold trap is switched off, all frozen substances are released in a short time and led to the detection device, which yields high and hence well detectable concentrations.

Such sampling tubes are used, for instance, to enable highly accurate determination of the air condition in submarines. This application is described in the article "Sampling of Submarine Atmospheres" by J. R. Wyatt, J. H. Callahan and T. J. Daley, in the SAE Technical paper Ser. No. 951656, pp. 1–6 (ISSN 0148-7191).

The sampling tubes can also be used in air pollution detector posts for measuring pollutions in the air in the street.

An important drawback of the known sampling tubes, also described already in the article mentioned, is formed by the pollution already present in the sampling tubes and which disturbs the measurements. In the above-mentioned article it is indicated that in the course of time unacceptable concentrations of benzene and toluene occur in the sampling tubes. In the case of detection involving an accuracy in the range of parts per trillion (ppt), the disturbance of the measurement caused by pollution in the sampling tubes is unacceptable. In the article mentioned, it is stated that in the future, experiments will be carried out with other adsorption materials in order to solve these problems. In the branch, apparently, the conviction is that the background disturbance of the measurements is caused by the adsorption material.

The insight underlying the present invention is that the pollution in the sampling tubes is not caused by the adsorption material itself but by the gas-permeable plugs between which the adsorption material is clamped. In the known sampling tubes, these gas-permeable plugs are made of glass wool. In order to avoid the glass wool being too brittle, it is produced while adding silicones. What is thus accomplished is that the glass wool, during the processing thereof, indeed remains glass wool and does not turn into powder. Upon heating of the sampling tubes, these silicones are liberated and disturb the measurement, and moreover the silicones adsorb substances that are liberated during the detection in an irregular manner, so that the gas chromatogram includes peaks that do not belong in it.

SUMMARY OF THE INVENTION

In order to solve these problems the sampling tube of the type described in the preamble is characterized according to the invention in that the plugs are manufactured from completely inert material and in that there is no non-inert material in the sampling tube.

Because the plugs are made of inert material and the sampling tube does not contain any non-inert material, such as, for instance, glass wool plugs, the background disturbance caused by substances not coming from the sampled air or the sampled gas is minimized. The improvement of the reliability of the measurement appears to be particularly significant in practice.

According to a further elaboration of the invention, the sampling tube is characterized in that the plugs are made from metal and are designed as a sieve. The metal can be, for instance, platinum, gold, silver, copper, stainless steel, or a metal alloy with similar inert properties.

According to an alternative further elaboration of the invention, the plugs are manufactured from pure ceramic or pure glass.

Further elaborations of the plug construction of the sampling tube according to the invention are described in the subclaims and are further clarified on the basis of an exemplary embodiment with reference to the drawings.

The closed sampling tube ends described in the preamble are formed, in a known sampling tube, by melting up the ends of the tube or by fitting special sealing caps on the ends.

A drawback of the sampling tubes with the melted-up ends is formed by the opening of these ends. This opening operation should be done with the necessary professional skill and care. Moreover, re-closing such sampling tubes requires a certain skill.

In view of the drawbacks of melting up as indicated above, meanwhile also sampling tubes have become known of which the glass tube has a constant outer diameter, the glass tube being closed off at the ends with a metal cap. The metal cap is provided with an end face and a cylindrical circumferential surface. The circumferential surface has an internal diameter greater than the external diameter of the glass tube and is provided on the inside with two O-rings. Apart from the fact that such caps are particularly costly, the sealing action thereof cannot be guaranteed under all circumstances. The coefficients of expansion of metal and glass differ considerably and upon increase of the temperature, the risk is not inconceivable that the sealing caps no longer seal properly and the adsorption material is prematurely contaminated with substances not coming from the gas to be examined or the air to be examined.

In order to solve these problems, a sampling tube comprising a glass tube, which sampling tube is filled, at least over a portion of the length of the tube, with an adsorption material, the adsorption material being confined between two gas-permeable plugs, and the ends of the glass tube being closed off with two sealing caps, is characterized according to the invention in that the sealing caps are manufactured from TEFLON® (trade name of the firm of Dupont; PTFE polytetrafluoroethene), the sealing caps comprising an end portion and a cylindrical stopper integrally connected therewith, which stopper, at least locally, has an external diameter receivable with a proper fit in the interior of the glass tube, the end portion having a diameter greater than the internal diameter of the glass tube.

Teflon has the particular property that it starts to flow under the influence of pressure and friction. When fitting a teflon cap according to the invention on the ends of the glass tube, this flow behavior arises, so that a hermetic seal is obtained. Moreover, teflon has a greater coefficient of expansion than glass, so that an increase of the ambient temperature leads to an increasingly tighter fit of the stopper in the glass tube and hence to an improved sealing.

In order to facilitate the connection of the sampling tube to a sampling device or in the detection arrangement, according to a further elaboration of the invention the sealing cap can be provided with an internal channel extending through the stopper and through at least a part of the end portion, the channel, at the location of the end portion, being closed off by a thin-walled end face wall portion. When placing the sampling tube, only this thin-walled end face wall portion needs to be pierced with a hollow needle, and the gas or the air to be sampled can be guided through the hollow needle, or the inert carrier gas can be guided through the sampling tube for the purpose of the detection. After the sampling has taken place, the pierced teflon sealing cap can simply be removed and be replaced by a new, as yet unpierced teflon sealing cap.

Further elaborations of the sampling tube with teflon sealing caps are described in the subclaims and are further clarified on the basis of an exemplary embodiment with reference to the drawing.

The invention further relates to a method for manufacturing a sampling tube according to the invention. According to the invention, for the adsorption material, TENAX powder is chosen, which is rinsed in methanol twice for four hours, whereafter the methanol is extracted from the TENAX powder by suction, whereafter the thus obtained TENAX material is gradually heated to at least about 250° C. and is maintained at this temperature for at least about 12 hours, while rinsing gas containing less than 10 ppm $O_2$ is blown through the TENX material, while the inert gas-permeable plugs designed as metal sieves are cleaned with the aid of methanol, and wherein subsequently the thus processed TENAX material is accommodated in the glass tube and the inert, gas-permeable plugs are fitted, whereafter the ends of the glass tube are closed off. Optionally, before the ends of the glass tube are closed off, the TENAX material can further be subjected to a vacuum one or more times, so that all contaminants are extracted therefrom. A thus manufactured sampling tube possesses particularly good properties and contains a negligible amount of substances that can disturb the measurements during the detection phase. The accuracy of the measurements performed utilizing the sampling tubes manufactured according to the method of the invention is therefore particularly high.

Presently, two exemplary embodiments of a sampling tube according to the invention as well as the method according to the invention will be described with reference to the drawings.

BRIEF DESCRIPTION OF THE DRAWINGS

FIG. 2A shows a sectional elevation with a detail of a sealing cap (FIG. 2B) and a detail of a plug (FIG. 2C) of a second exemplary embodiment;

DETAILED DESCRIPTION OF THE INVENTION

Figures 1A, 1B:
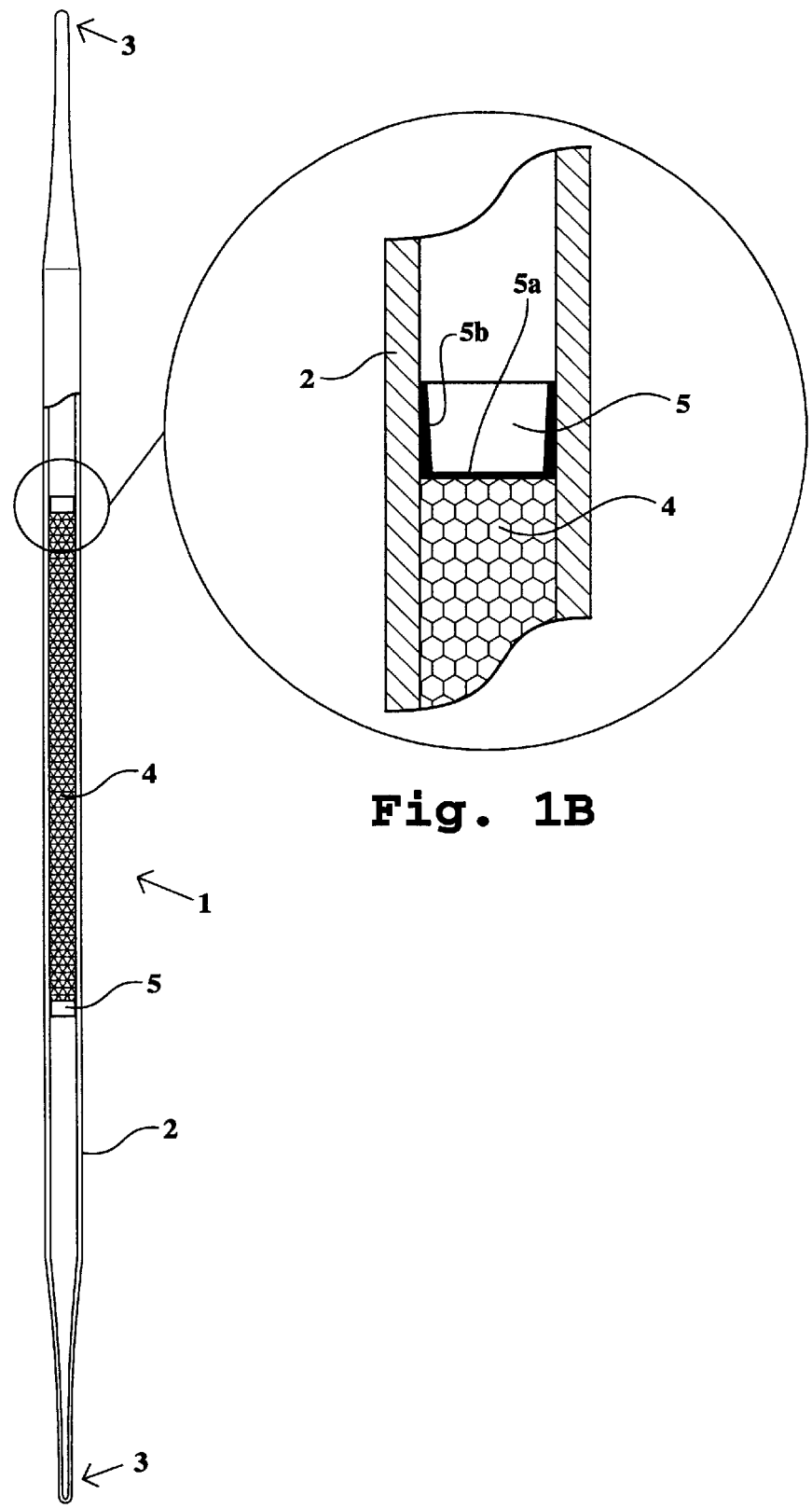
FIG. 1A shows a sectional elevation with a detail (FIG. 1B) of a plug of a first exemplary embodiment.

The sampling tube 1 shown in both FIG. 1 and FIG. 2 comprises a glass tube 2 with two closed ends 3. The sampling tube is filled, at least over a portion of the length of the tube 2, with an adsorption material 4. The adsorption material is confined between two gas permeable plugs 5.

According to the invention, the plugs 5 are manufactured from completely inert material, and there is no non-inert material, such as, for instance, glass wool plugs, in the tube. In the exemplary embodiments shown in the drawings, the plugs 5 are manufactured from metal and designed as a sieve 5. Suitable metals from which the sieve 5 can be manufactured are, for instance, platinum, gold, silver, copper, or stainless steel, or a metal alloy with such inert properties. However, it is also very well possible for the plugs 5 to be manufactured from pure ceramic or pure glass.

In the present exemplary embodiments, the metal sieve 5 is designed as a cap with a gas-permeable end face 5a and a cylindrical circumferential surface 5b, extending substantially perpendicularly to the end face. The external diameter of the cylindrical surface 5b with respect to the internal diameter of the glass tube 2 is such that the metal sieve 5 is receivable in the glass tube 2 with a clamping fit, whereby the end face 5a, in mounted condition of the sieve, abuts against the adsorption material 4, and the cylindrical surface 5b extends in the direction away from the adsorption material 4.

In the exemplary embodiment shown, for the adsorption material 4, TENAX® (trade name of the firm of AKZO; polyphenylene oxides) in powder form was chosen. However, for the adsorption material 4, other substances can be chosen too, such as activated carbon containing materials in powdered or granular form, such as carbograph™, carbosieve™ and carbotrap™, or other adsorbing powder or granular materials such as silica gel, deactivated aluminum and the like.

In the exemplary embodiment shown in FIG. 1, the ends 3 of the glass tube 2 are sealed in that they have been melted up.

In the exemplary embodiment shown in FIG. 2, the ends 3 of the glass tube 2 are closed off with the sealing caps 6 which are manufactured from TEFLON® (trade name of the firm of Dupont; PFTE Polytetrafluoroethene). The sealing caps 6 are provided with an end portion 7 and a cylindrical stopper 8 integrally connected therewith, which stopper, at least locally, has an external diameter receivable with a proper fit in the interior of the glass tube 2. The end portion 7 has a diameter greater than the internal diameter of the glass tube 2.

In the present exemplary embodiment, the sealing cap is provided with an internal channel 9, which extends through the stopper 8 and through at least a portion of the end portion 7. At the end portion 7 the channel 9 is closed off by a thin-walled end face wall portion 10. The cylindrical stopper 8 has a circumferential surface of which the diameter is variable in that in the circumferential surface a number of annular recesses 11 are provided which have a diameter smaller than the above-mentioned external diameter of the other parts of the circumferential surface. It will be clear that sealing caps 6 of such design can also be profitably used in the sampling tubes known from the prior art.

Because upon prolonged storage, contaminations may yet diffuse along the TEFLON caps to the interior of the tube, it is possible, in accordance with a further elaboration of the invention, for the sampling tube provided with caps to be accommodated in a melted-up glass tube with a breaking edge. When the sampling tube is to be put to use, the melted-up tube can be opened via the breaking edge, so that the sampling tube is made available.

For manufacturing the sampling tubes represented in FIGS. 1 and 2, the TENAX powder 4 is rinsed in methanol twice for four hours using Soxhlet extraction. Then the methanol is extracted from the TENAX powder by suction. Thereafter the thus obtained TENAX material is gradually heated to at least about 250° C. and held at this temperature for at least about 12 hours, while rinsing gas containing less than 10 ppm $O_2$ is blown through the TENAX material. Also, the inert gas-permeable plugs 5 designed as sieves are cleaned with the aid of methanol. Subsequently, the thus processed TENAX material is accommodated in a glass tube 2 and the inert, gas-permeable plugs 5 are fitted. Finally, the ends of the glass tube are closed off. Closing the ends 3 of the glass tube 2 can take place, for instance, using sealing caps 6 made of TEFLON® (trade name of the firm of Dupont; PFTE Polytetrafluoroethene) and which are designed in the manner as described hereinabove with reference to FIG. 2. The closure of the ends 3 of the glass tube 2, however, can also take place by melting up the ends 3, which leads to a sampling tube 1 as shown in FIG. 1.

Figure 3:
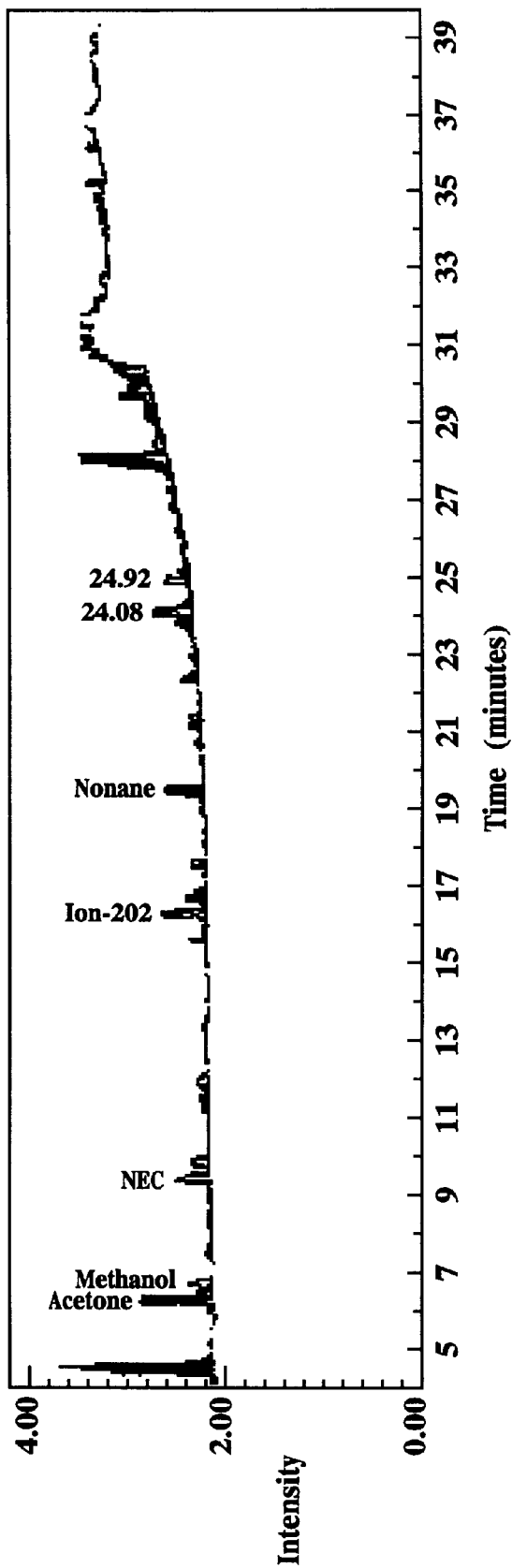
FIG. 3 shows a gas chromatogram of an unsampled prior art sampling tube.
Figure 4:
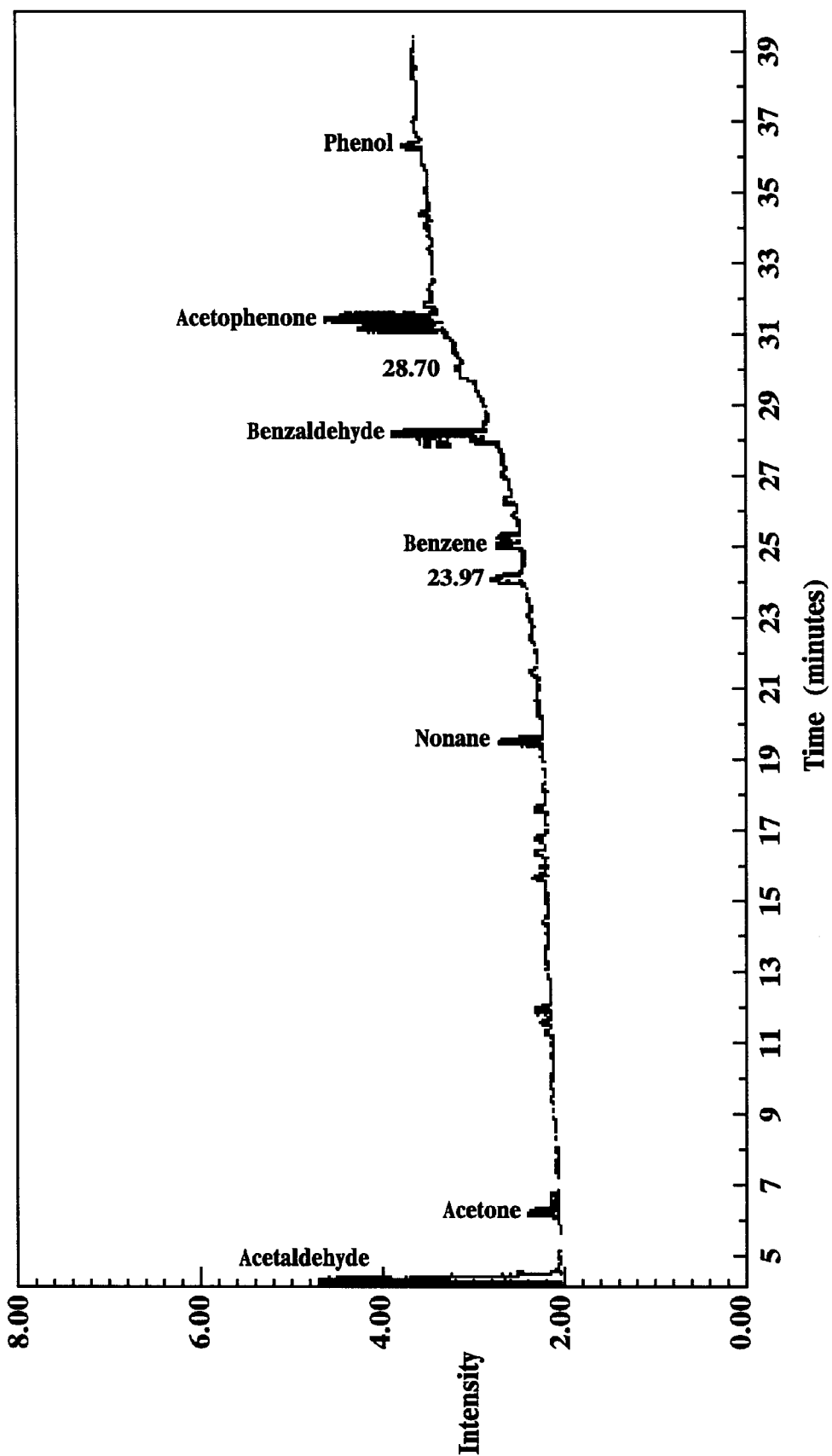
FIG. 4 shows a gas chromatogram of an unsampled sampling tube according to the invention.

Sampling tubes 1 thus manufactured and designed have superior properties. While with the known sampling tubes in the gas chromatographic detection an objectionable background disturbance occurred, which greatly hindered the reliability of the detection, in the sampling tubes according to the invention this background disturbance has been minimized to a level that is quite acceptable. To illustrate the difference between the presence of plugs 5 which are made from glass wool and plugs 5 which are made from inert material, reference is made to FIGS. 3 and 4. Both figures show a gas chromatogram of two unsampled, that is, new sampling tubes. The two sampling tubes have been manufactured in the same manner according to the same protocol. The only difference resides in the plugs 5 which confine the adsorption material 4. The sampling tube 1 of which the gas chromatogram is shown in FIG. 3 is provided with plugs 5 which are made from glass wool. So this is not a sampling tube according to the invention. The sampling tube 1 of which the gas chromatogram is represented in FIG. 4 is provided with plugs 5 which are made of inert material, in particular from stainless steel. The differences between the two gas chromatograms show very clearly the considerable reduction of the presence of undesired substances in the sampling tube 1 according to the invention (FIG. 4). Owing to this considerable reduction of undesired substances, the measurements in the detection phase will be considerably more accurate and not be disturbed, or hardly so, by background disturbances.

It will be clear that the invention is not limited to the exemplary embodiment described, but that various modifications are possible within the scope of the invention.

It is claimed:

1. A sampling tube (1) comprising a glass tube (2) with two ends (3) which can be opened for collection and for analysis of a sample and closed for storage of the sample, the sampling tube (1) being filled, at least over a portion of the length of the tube, with an adsorption material (4), the adsorption material (4) being confined between two gas-permeable plugs (5) which are manufactured from a material other than glass wool, said material being completely inert such that said tube prior to sample collection contains no components capable of being liberated on heating in the sampling tube.

2. The sampling tube of claim 1, characterized in that the plugs (5) are manufactured from metal and are designed as a sieve.

3. The sampling tube of claim 2, characterized in that the sieve (5) is manufactured from a material selected from the group consisting of platinum, gold, silver, copper, stainless steel, and an inert metal alloy.

4. The sampling tube of claim 2, characterized in that the metal sieve (5) is designed as a cap with a gas-permeable end face (5a) and a cylindrical surface (5b) extending substantially perpendicularly to the end face, the external diameter of the cylindrical surface (5b) with respect to the internal diameter of the glass tube (2) being such that the metal sieve (5) is receivable in the glass tube (2) with a clamping fit, whereby the end face (5a), in the mounted condition of the sieve (5), abuts against the adsorption material (4), and the cylindrical surface (5b) extends in the direction away from the adsorption material (4).

5. The sampling tube of claim 1, characterized in that the plugs (5) are manufactured from pure ceramic or pure glass.

6. The sampling tube of claim 1, characterized in that the adsorption material (4) comprises polyphenylene oxides in powder or granular form.

7. The sampling tube of claim 1, characterized in that the adsorption material (4) is comprised of an adsorbing material in powder or granular form.

8. The sampling tube of claim 1, characterized in that the ends of the glass tube (2) are sealed closed by melting each end.

9. The sampling tube of claim 1, characterized in that the adsorption material (4) is comprised of an adsorbing material selected from the group consisting of activated carbon, silica gel and deactivated aluminum.

* * * * *